United States Patent [19]
Anderson et al.

[11] Patent Number: 6,027,507
[45] Date of Patent: Feb. 22, 2000

[54] LEG LENGTH GAUGE FOR TOTAL HIP SURGERY

[75] Inventors: James M. Anderson, Mentone, Ind.; William J. Bose, Mobile, Ala.; David Kaufman, New Haven, Ind.

[73] Assignee: Innomed, Inc., Savannah, Ga.

[21] Appl. No.: 09/070,237

[22] Filed: Apr. 30, 1998

[51] Int. Cl.$^7$ .................................................. A61B 17/56
[52] U.S. Cl. ............................................. 606/102; 606/86
[58] Field of Search ................................ 606/54, 86, 87, 606/88, 89, 90, 102

[56] References Cited

U.S. PATENT DOCUMENTS

| | | | |
|---|---|---|---|
| 5,334,205 | 8/1994 | Cain | 606/86 |
| 5,688,283 | 11/1997 | Knapp | 606/102 |
| 5,704,941 | 1/1998 | Jacober et al. | 606/87 |

*Primary Examiner*—Michael Buiz
*Assistant Examiner*—Daphna Shai
*Attorney, Agent, or Firm*—Lundy and Associates

[57] ABSTRACT

A leg length gauge for use during hip joint replacement surgery to insure that the overall length of the patient's leg subsequent to the surgery is substantially the same as it was prior to the surgery. A first pin is inserted into a patient's ilium and a second pin is inserted into the patient's femur. A removable gauge including an adjustably coupled pair of members having pin receiving apertures for receiving the first and second pins is positioned on the pins. One member includes a base portion provided with one of said pin receiving apertures and having an elongated leg extending from the base portion. The other member is provided with the other pin receiving aperture and includes a transverse aperture for receiving the elongated leg. The elongated leg is selectively adjustably secured within the transverse aperture by tightening a thumbscrew. When properly oriented, the first pin extends generally vertically from the ilium, the second pin extends generally vertically from the femur and the elongated leg extends generally horizontally between the base portion and the other member.

15 Claims, 3 Drawing Sheets

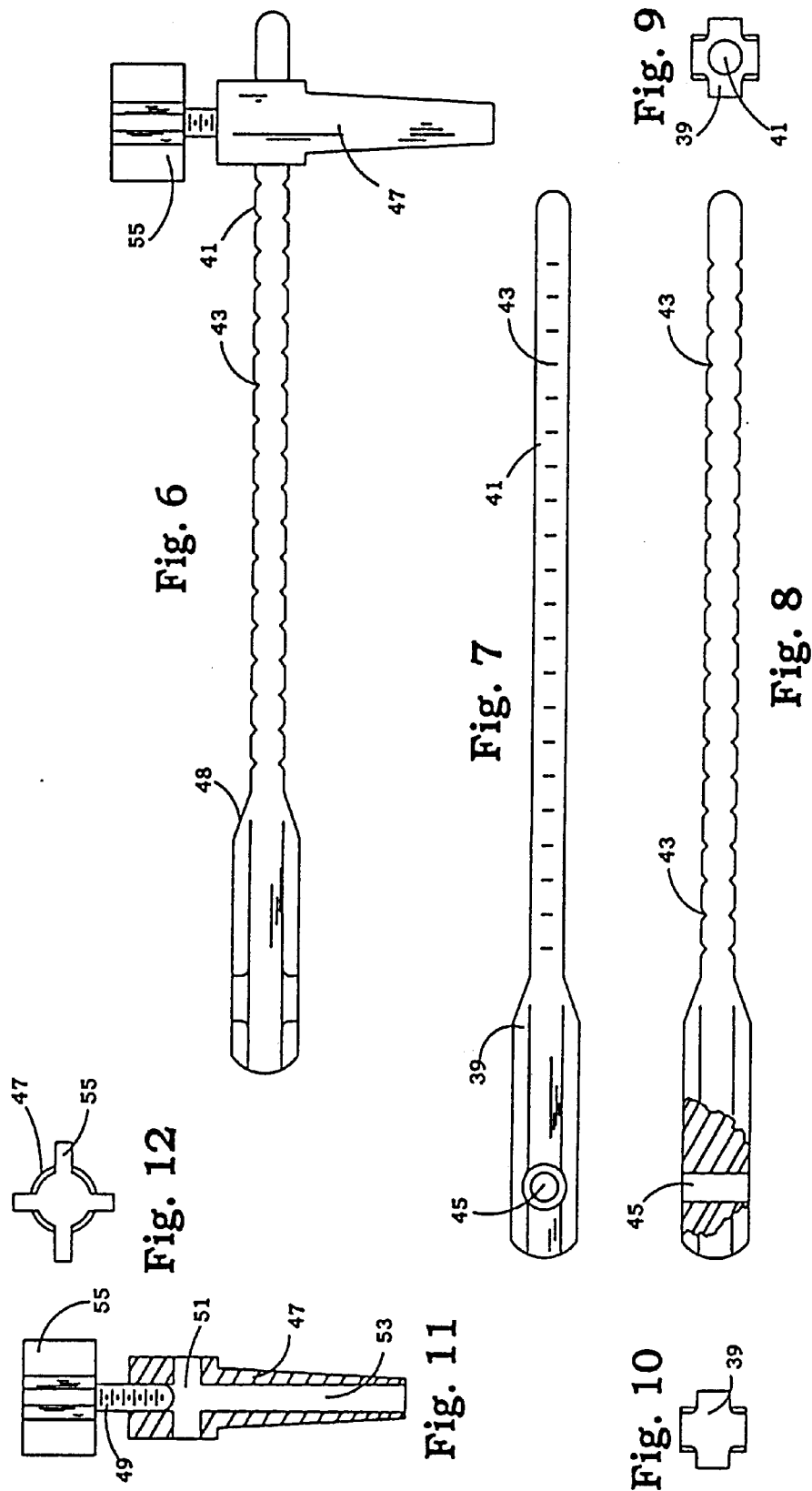

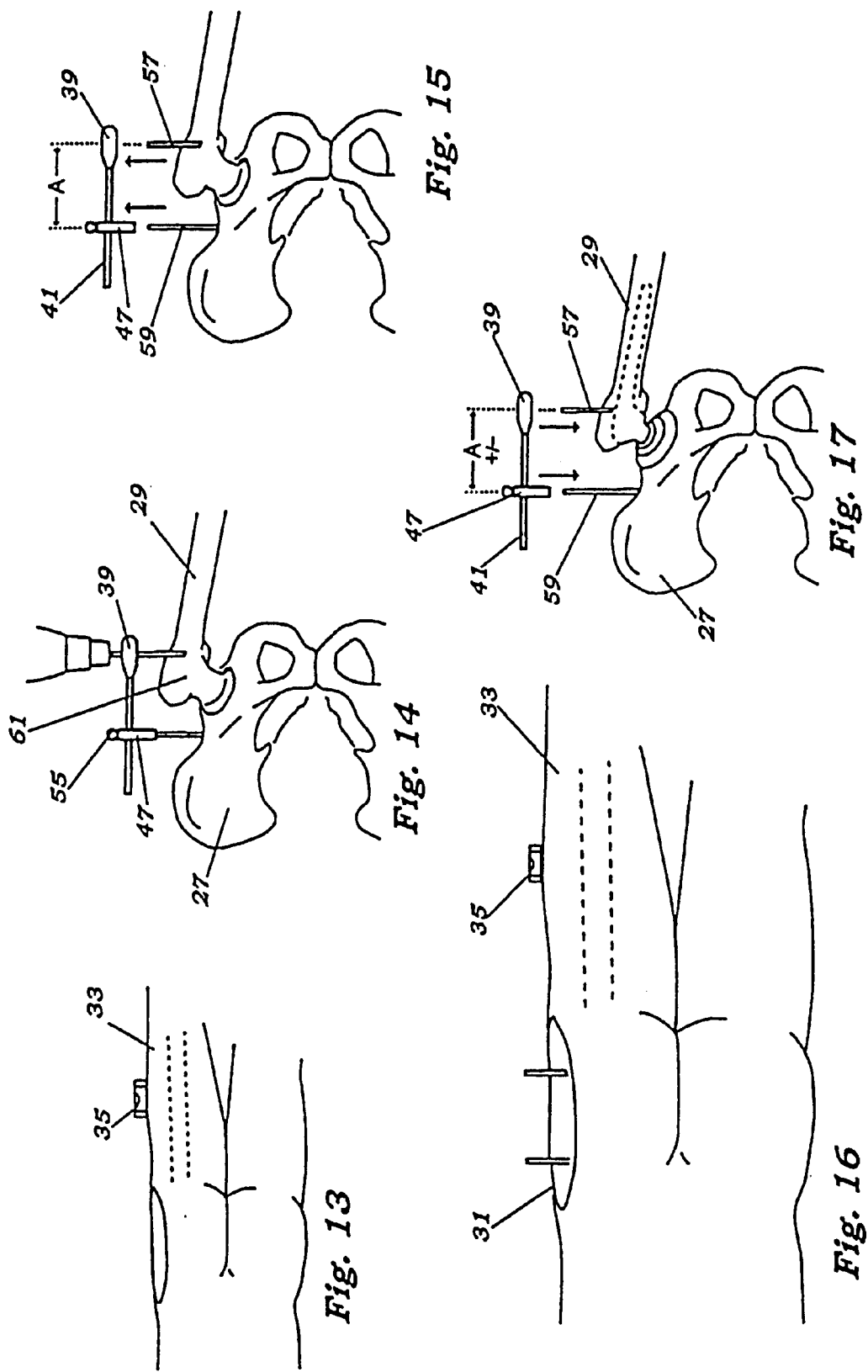

LEG LENGTH GAUGE FOR TOTAL HIP SURGERY

SUMMARY OF THE INVENTION

The present invention relates generally to a measuring device to be utilized during hip replacement surgery to insure, so far as possible, that the overall length of the patient's leg is not changed by that replacement surgery.

The problems associated with such changes in overall leg length are well known and several prior attempts to control leg length changes have been made.

The Fishbane U.S. Pat. No. 5,122,145 teaches a measuring technique where two Steinmann pins are placed in holes drilled in the patient's ilium and a third is placed in a hole drilled in the femur. The technique requires leveling the instrument and the taking of two measurements before surgery and at least the same two measurements after surgery. The measuring device of this patent includes a pivotable arm and two calibrated members adjustably joined orthogonally to one another. The device is made of a metal compatible with known sterilization methods for surgical instruments. The U.S. Pat. No. 5,318,571 to Benson uses a flexible cable somewhat less precisely for similar measurements. There is an extensive list of relevant literature recited in the introductory portions of this patent.

Among the several objects of the present invention may be noted the provision of a gauge to be used during hip joint replacement surgery to make sure the patient's leg length after surgery is the same as it was before; the provision of an economical, disposable gauge for insuring overall leg length constancy before and after surgery; the provision of a leg length gauge which eliminates the need to record and subsequently refer to measurements; and the provision of a simplified technique for monitoring leg length during hip replacement surgery. These as well as other objects and advantageous features of the present invention will be in part apparent and in part pointed out hereinafter.

In general, a process of performing hip joint replacement surgery incorporates an improved method of maintaining the original spacing between the ilium and femur by positioning the femur in a relatively level position and inserting a first pin into the femur to extend generally vertically therefrom A second pin is inserted into the ilium to extend generally vertically therefrom. A removable replica of the spacing between the first and second pins is created and removed from the pins. The hip joint joining the ilium and femur is replaced and the femur is returned to the relatively level position. The replica is then replaced on the pins to confirm that the original spacing between the femur and ilium has been maintained. The removable replica is created by use of a gauge including an adjustably coupled pair of members each having a pin receiving aperture. One gauge member comprises a member having an elongated leg adjustably coupled to the other member by a thumbscrew and a base portion provided with the pin receiving aperture. Creating the replica includes loosening the thumbscrew, positioning one member with the first pin received in its pin receiving aperture, positioning the other member with the second pin received in its pin receiving aperture, and tightening the thumbscrew to fix the separation between the members.

BRIEF DESCRIPTION OF THE DRAWING

FIG. 6 is a side elevation view of a modified leg length gauge according to the present invention;

FIG. 7 is a top plan view of one of the gauge members of the leg length gauge of FIG. 6;

FIG. 8 is a side elevation view, partially in cross-section of the one gauge member of FIG. 7;

FIG. 9 is an end elevation view of the gauge member of FIG. 8 from the right side thereof;

FIG. 10 is an end elevation view of the gauge member of FIG. 8 from the left side thereof;

FIG. 11 is a side elevation view, partially in cross-section of the other gauge member of FIG. 6;

FIG. 12 is a top plan view of the other gauge member of FIG. 11;

FIG. 13 is a rear elevation view of a patient illustrating use of the level in initially positioning the patient's leg;

FIG. 14 is a rear elevation view illustrating application of the leg length gauge to the skeletal members of The patient;

FIG. 15 is a view similar to FIG. 14, but illustrating removal of the leg length gauge;

FIG. 16 is a rear elevation view of a patient illustrating use of the level in repositioning the patient's leg subsequent to joint replacement; and FIG. 17 is a view similar to FIG. 14 illustrating reapplication of the leg length gauge subsequent to joint replacement.

Corresponding reference characters indicate corresponding parts throughout the several views of the drawing.

The exemplifications set out herein illustrate a preferred embodiment of the invention in one form thereof and such exemplifications are not to be construed as limiting the scope of the disclosure or the scope of the invention in any manner.

DESCRIPTION OF THE PREFERRED EMBODIMENT

Figure 1:
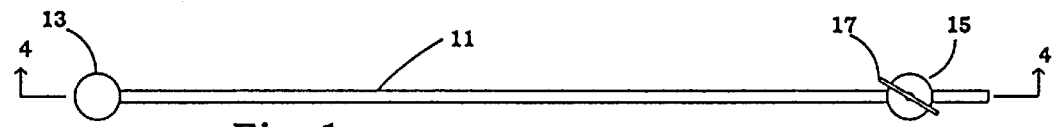
FIG. 1 is a top plan view of a leg length gauge for total hip surgery.
Figure 2:
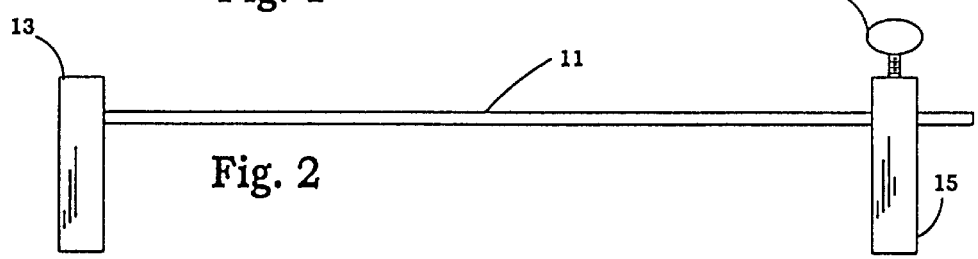
FIG. 2 is a side elevation view of the gauge of FIG. 1.
Figure 3:
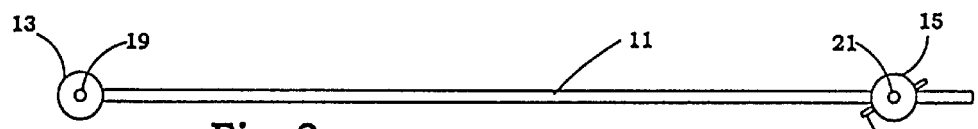
FIG. 3 is a bottom plan view of the gauge of FIGS. 1 and 2.
Figure 4:
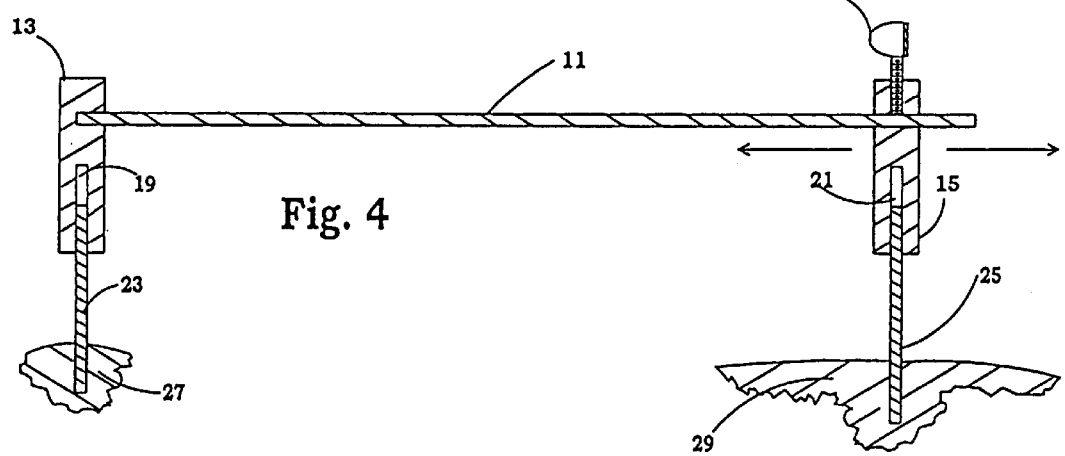
FIG. 4 is a cross-sectional view along the line 4—4 of FIG. 1 and further illustrating the gauge applied to a patient.

The drawings illustrate a gauge used during hip joint replacement surgery to make sure the patient's leg length after surgery is the same as it was before. The gauge has a pair of plastic rods 13 and 15 interconnected by a spanning rod 11. Rods 11 and 13 are permanently connected while rod 15 is free to slide back and forth along the spanning rod 11 so long as the thumbscrew 17 is not tightened. As seen in FIGS. 3 and 4, there are a pair of pin accepting holes 19 and 21 in the bottoms of the rods 13 and 15.

To apply the leg length gauge for use during hip joint replacement surgery, a first pin 23 is inserted into a patient's ilium 27 extending generally vertically therefrom and a second pin 25 is inserted into a patient's femur 29, again, extending generally vertically. The, removable gauge includes an adjustably coupled pair of members 13 and 15 having pin receiving apertures 19 and 21 for receiving the first and second pins. One member 13 includes a base portion provided with the pin receiving aperture 19 and has an elongated leg 11 extending generally horizontally from the base portion. The other member 15 is provided with the other of said pin receiving apertures 21 and includes a transverse aperture which is elongated in a direction generally orthogonal to the direction of elongation of aperture 21 for receiving the elongated leg. A replica of the separation between the two pins is created by the location where the elongated leg is secured within the transverse aperture by tightening thumbscrew 17. The members are made of plastic and the elongated leg 11 has a length to width ratio sufficiently large to allow flexibility of the leg while maintaining the distance between the apertures 19 and 21 substantially unchanged.

Figure 5:
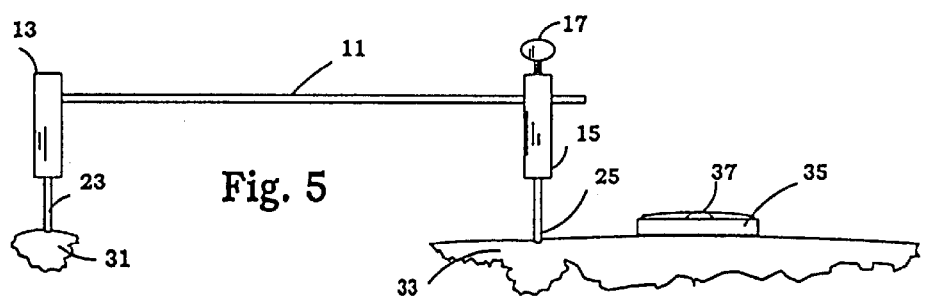
FIG. 5 is a side elevation view similar to FIG. 2, but showing the gauge applied to a patient and illustrating leveling of the patient's leg.

Typically, the patient is positioned on his side. In FIGS. 4 and 5, the pin 23 is inserted into the hip bone 27 with a portion thereof extending from the hip 31, and another pin 25 is inserted into the femur or upper leg bone 29. Again, this pin 25 extends beyond the surface of the patient's leg 33. These pins may be inserted into pre-drilled holes or may be threaded and form their own hole during insertion. The level 35 is placed on the patient's leg and the leg leveled if necessary. The level provides a means for monitoring the inclination of the femur. The leveling will be repeated for each gauge measurement to ensure consistency. The gauge is positioned on the pins with the thumbscrew 17 loose. With the leg in a level position, the thumbscrew 17 is tightened thereby providing an accurate replica of the separation between the pins 23 and 25. The gauge is removed, one or both of the pins may be left in place, and surgery commenced. After the new joint is in place, the leg is again leveled by replacing level 35 on the patient's leg 33 and changing leg elevation until the air bubble 37 is centered. The gauge applied to the pins to determine if the leg has been lengthened or shortened. The gauge may be applied periodically during surgery to make sure the overall leg length is being maintained.

In FIG. 6, a recently developed and presently preferred embodiment is illustrated. Here, a modified L-shaped member has an enlarged fluted base portion 39 and an elongated leg 41 extending therefrom. Except as noted, the members 43 and 47 of FIG. 6 are essentially circular in cross-section throughout their length. A series of indentations 43 of, for example, 2 millimeter spacing, provide the option for calibrating the gauge if desired. The other member 47 which is adjustably positionable along the elongated leg 41 is similar to that illustrated in FIGS. 1–5, however, the thumb screw 55 is a molded plastic and the leg 47 is tapered somewhat while remaining circular in cross-section. In this preferred embodiment, the overall gauge length is about 6 inches with the fluted base 39 being about three-eights of an inch in diameter and the distance between aperture 45 and the beginning of the indentations 41 being about 1¼ inches. The distance from the aperture 45 to the far end of the taper 48 is about one inch. The elongated leg 41 is about one eighth of an inch in diameter allowing some flexibility relative to the base portion 39. The calibrating indentations extend for slightly less than four inches along the elongated leg.

Like the embodiment of FIGS. 1–5, this second embodiment of a removable gauge includes an adjustably coupled pair of members each having a pin receiving aperture 45 or 53 for receiving the first and second pins 57 or 59 respectively. The member shown in FIGS. 7–10 includes the base portion 39 provided with the pin receiving apertures 45 and having an elongated leg 41 extending from the base portion. The other member of FIGS. 11 and 12 is provided with the other of the pin receiving apertures 53 and includes a transverse aperture 51 for receiving the elongated leg 41. The elongated leg 41 is selectively adjustably secured within the transverse aperture 51 by tightening thumbscrew 55.

The method of operation of the invention should now be clear. The following is one preferred protocol for using the leg length measuring device. After the approach to the hip has been made and prior to dislocation of the hip, a one quarter inch or five-sixteenth inch, threaded pin (which has been cut to half length) is placed over a sleeve, through the hip abductors and drilled into the ilium of the pelvis. The threaded Steinmann pin is drilled to both tables of the ilium at an angle perpendicular to the floor. This gives us a fixed point on the pelvis for our measuring device. The hip is then held in the neutral position using the level. A smooth quarter inch or five-sixteenth inch Steinmann pin is then drilled through the lateral aspect of the femur, just inferior to the greater trochanter at the origin of the vastus lateralis musculature. A bovie mark is made at this drill mark for identification later in the procedure. Again, with the leg held in the neutral position using the level, the original leg length is measured using our device. The smooth Steinmann pin is then removed from the femur. The threaded pin in the pelvis is left in position and the total hip arthroplasty is performed. Once the trial components are in position the hip is reduced. Again the leg position is reproduced using the level and the smooth Steinmann pin (which has been cut in half) is placed in the same drill hole in the femur that was made earlier in the procedure. Leg length is then remeasured using our measuring device and leg length can then be adjusted if necessary. The final components are then placed into the hip and remeasurement of the hip arthroplasty with the final components can also be performed if desired.

A very similar preferred protocol is now described with specific reference to FIGS. 13–17 and the leg length gauge of FIG. 6. The leg length gauge is first used after the hip joint is completely exposed, just prior to dislocation of the femoral head. The hip joint is placed in maximum extension, zero abduction and neutral rotation. The leveling device 35 can be used to confirm this position As illustrated in FIG. 13. An ⅛ inch pin 59 is placed into the ilium 27. The sliding portion 47 of the Leg length gauge is placed on the ilium pin 59. A second pin is passed through the hole 45 on the fixed end 39 of the gauge and drilled into the greater trochanter 61 as seen in FIG. 14. The sliding portion 47 of the gauge is locked in place by tightening the thumb screw 55. The locked gauge and the pin 57 from the greater trochanter 61 are then removed as illustrated in FIG. 15. The pin hole on the greater trochanter should be marked and the pin 59 in the ilium is left in place. It is important that the gauge remain unchanged in its locked position while the total hip replacement is carried out.

When the trials or implants are in position as in FIG. 16, the hip joint is placed in the original position of maximum extension, zero abduction, neutral rotation. The leveling device 35 can be used to reproduce the original position of the leg. The ⅛ inch trochanter pin 57 is reinserted into its original hole. The locked Leg length gauge is replaced onto the pins to determine if the distance between the two points has been altered or needs appropriate adjustment as illustrated in FIG. 17. If it is necessary to move the sliding portion 41 of the gauge to place it on pin 59, the locked position should be marked on the gauge stem for reference before loosening the thumbscrew 55. Any change in leg length can then be measured and adjustments in femoral neck lengths made as deemed appropriate.

In summary, the leg length gauge of the invention has a number of advantages over known prior leg length measuring schemes. It is disposable in the sense that it is used during one operation only and then discarded rather than being sterilizes for reuse. The gauge is far less expensive than known prior devices. Due to this economy of manufacture it may be used during a single replacement surgery and discarded, thus avoiding the problems of re-sterilization characteristic of prior gauges.

From the foregoing, it is now apparent that a novel disposable leg length gauge and associated measuring technique have been disclosed meeting the objects and advantageous features set out hereinbefore as well as others, and that numerous modifications as to the precise shapes, configurations and details may be made by those having ordinary skill in the art without departing from the spirit of the invention or the scope thereof as set out by the claims which follow.

What is claimed is:

1. A leg length gauge for use during hip joint replacement surgery to insure that the overall length of the patient's leg subsequent to the surgery is substantially the same as it was prior to the surgery comprising:

a first pin adapted to be inserted into a patient's ilium;

a second pin adapted to be inserted into a patient's femur;

a first member having a leg, said first member including an aperture for receiving one of said first and second pins;

a second member including a first second member aperture for receiving the other of the first and second pins, and a second second member aperture for receiving said first member leg; said leg extending generally perpendicularly of said first and second pins; and means for selectively adjustably securing said first member leg within said second second member aperture.

2. The leg length gauge of claim 1 wherein said first second second member aperture and said second second member aperture comprise generally cylindrical holes elongated in directions generally orthogonal to one another.

3. The leg length gauge of claim 1 further comprising means for monitoring the inclination of the femur.

4. The leg length gauge of claim 3 wherein, with the pins received within the first and second members and a predetermined femur inclination, the longer leg may be secured within the second aperture, the gauge removed from the pins, hip joint replacement surgery performed, femur inclination replicated and the gauge repositioned on the pins to thereby allow replication of the separation between the two pins and therefor also the original spacing between the ilium and femur.

5. The leg length gauge of claim 1 wherein the means for adjustably selectively securing comprises a thumbscrew threadedly received in the second member and movable therein to selectively engage and secure the longer leg within the second aperture.

6. The leg length gauge of claim 1 wherein the L-shaped member and second member are made of plastic and the longer leg has a length to width ratio sufficiently large to allow flexibility of the longer leg while maintaining the distance between the shorter leg and the second member substantially unchanged.

7. In the process of performing hip joint replacement surgery, the improved method of maintaining the original spacing between the ilium and femur comprising:

positioning the femur in a relatively level position;

inserting a first pin into the femur to extend generally vertically therefrom;

inserting a second pin into the ilium to extend generally vertically therefrom;

creating a removable replica of the spacing between the first and second pins;

removing the replica from the pins;

replacing the joint joining the ilium and femur;

repositioning the femur in a relatively level position; and replacing the replica on the pins to confirm that the original spacing between the femur and ilium has been maintained.

8. The method of claim 7 wherein the removable replica is created by use of a gauge including an adjustably coupled pair of members each having a pin receiving aperture.

9. The method of claim 7 wherein one gauge member comprises a member having an elongated leg adjustably coupled to the other member by a thumbscrew and a base portion provided with the pin receiving aperture, the method of creating including loosening the thumbscrew, positioning one member with the first pin received in its pin receiving aperture, positioning the other member with the second pin received in its pin receiving aperture, and tightening the thumbscrew to fix the separation between the members.

10. A leg length gauge for use during hip joint replacement surgery to insure that the overall length of the patient's leg subsequent to the surgery is substantially the same as it was prior to the surgery comprising:

a first pin adapted to be inserted into a patient's ilium;

a second pin adapted to be inserted into a patient's femur;

a removable gauge including an adjustably coupled pair of members having pin receiving apertures for receiving said first and second pins;

one member including a base portion provided with one of said pin receiving apertures and having an elongated leg extending from the base portion;

the other member being provided with the other of said pin receiving apertures and including a transverse aperture for receiving the elongated leg; said leg extending generally perpendicularly of said first and second pins; and means for selectively adjustably securing the elongated leg within the transverse aperture.

11. The leg length gauge of claim 10 wherein the other member pin receiving aperture and transverse aperture comprise generally cylindrical holes elongated in directions generally orthogonal to one another.

12. The leg length gauge of claim 10 further comprising means for monitoring the inclination of the femur.

13. The leg length gauge of claim 12 wherein, with the pins received within the members and a predetermined femur inclination, the elongated leg may be secured within the transverse aperture, the gauge removed from the pins, hip joint replacement surgery performed, femur inclination replicated and the gauge repositioned on the pins to thereby allow replication of the separation between the two pins and therefor also the original spacing between the ilium and femur.

14. The leg length gauge of claim 10 wherein the means for adjustably selectively securing comprises a thumbscrew threadedly received in the other member and movable therein to selectively engage and secure the elongated leg within the transverse aperture.

15. The leg length gauge of claim 10 wherein the members are made of plastic and the elongated leg has a length to width ratio sufficiently large to allow flexibility of the elongated leg while maintaining the distance between the base portion and the other member substantially unchanged.

* * * * *